(12) United States Patent
Chan et al.

(10) Patent No.: US 9,329,130 B2
(45) Date of Patent: May 3, 2016

(54) SYSTEMS AND METHODS FOR COUNTING CELLS AND BIOMOLECULES

(75) Inventors: Leo L. Chan, North Andover, MA (US); Peter Li, North Andover, MA (US)

(73) Assignee: Nexcelom Bioscience LLC, Lawrence, MA (US)

( * ) Notice: Subject to any disclaimer, the term of this patent is extended or adjusted under 35 U.S.C. 154(b) by 751 days.

(21) Appl. No.: 13/519,282

(22) PCT Filed: Jan. 11, 2011

(86) PCT No.: PCT/US2011/020766
§ 371 (c)(1),
(2), (4) Date: Jan. 3, 2013

(87) PCT Pub. No.: WO2011/088014
PCT Pub. Date: Jul. 21, 2011

(65) Prior Publication Data
US 2013/0099120 A1    Apr. 25, 2013

Related U.S. Application Data

(60) Provisional application No. 61/294,236, filed on Jan. 12, 2010.

(51) Int. Cl.
*G01N 21/64* (2006.01)
*G01N 15/14* (2006.01)
*G01N 33/50* (2006.01)
G01N 21/3581 (2014.01)
G01J 5/10 (2006.01)

(52) U.S. Cl.
CPC ........ *G01N 21/6486* (2013.01); *G01N 15/1463* (2013.01); *G01N 21/6428* (2013.01); *G01N 21/6456* (2013.01); *G01N 33/5005* (2013.01); *G01J 5/10* (2013.01); *G01N 21/3581* (2013.01); *G01N 21/64* (2013.01); *G01N 2015/1486* (2013.01)

(58) Field of Classification Search
CPC ....... G01J 5/10; G01N 21/3581; G01N 21/64; G01N 21/6486
See application file for complete search history.

(56) References Cited

U.S. PATENT DOCUMENTS

| | | | |
|---|---|---|---|
| 5,355,215 A * | 10/1994 | Schroeder et al. | 356/317 |
| 8,901,514 B2 * | 12/2014 | Lee | 250/459.1 |
| 8,947,518 B2 * | 2/2015 | Kiyota et al. | 348/79 |
| 2002/0155617 A1 * | 10/2002 | Pham et al. | 436/165 |
| 2009/0179159 A1 * | 7/2009 | Yamada | 250/459.1 |
| 2009/0212242 A1 * | 8/2009 | Yamada | 250/580 |
| 2009/0263328 A1 * | 10/2009 | Nakajima et al. | 424/9.6 |
| 2013/0092821 A1 * | 4/2013 | Ozcan et al. | 250/208.1 |

* cited by examiner

*Primary Examiner* — Christine Sung
(74) *Attorney, Agent, or Firm* — Milstein Zhang & Wu LLC

(57) ABSTRACT

The invention generally relates to analytical and monitoring systems useful for analyzing and measuring cells and biological samples. More particularly, the invention relates to systems and methods for imaging, measuring, counting, analyzing, and monitoring microscopic particles such as cells and biological molecules in solution samples.

15 Claims, 10 Drawing Sheets

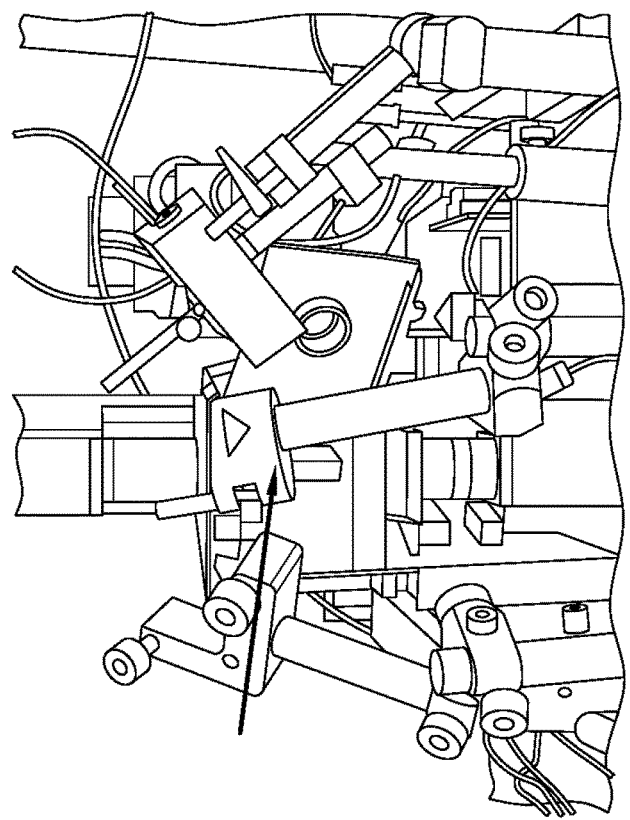
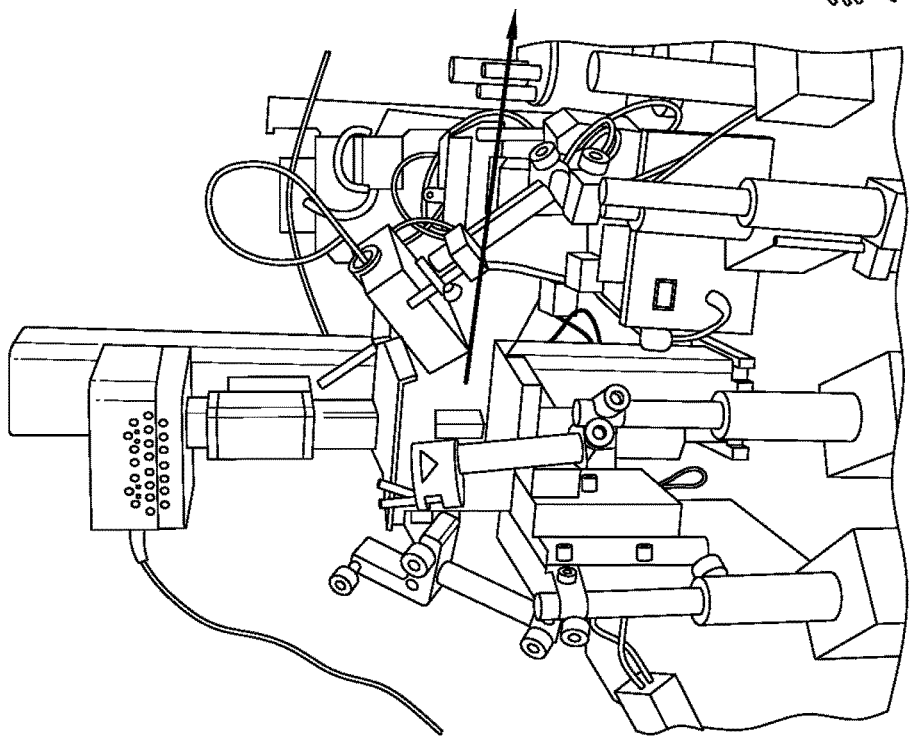
FIG. 4A
FIG. 4B

SYSTEMS AND METHODS FOR COUNTING CELLS AND BIOMOLECULES

PRIORITY CLAIMS

This application is the national phase of PCT/US11/20766, filed Jan. 11, 2011, which claims the benefit of priority from U.S. Provisional Application Ser. No. 61/294,236, filed Jan. 12, 2010, the entire content of each of which is incorporated herein by reference for all purposes.

TECHNICAL FIELDS OF THE INVENTION

The invention generally relates to analytical and monitoring systems useful for analyzing and measuring cells and biological samples. More particularly, the invention relates to systems and methods for imaging, measuring, counting, analyzing, and monitoring microscopic particles such as cells and biological molecules in solution samples.

BACKGROUND OF THE INVENTION

An important aspect in the fields of medical diagnostics and biomedical research involves detection, identification, quantification, and characterization of various cells and biomolecules of interest through testing of biological samples such as blood, spinal fluid, cell culture and urine. Healthcare providers and biomedical researchers routinely analyze such biological samples for the microscopic presence and concentrations of cells and biomolecules.

Fluorescence microscopy, fluorescent plate reader, and flow cytometry are traditionally used for fluorescence detection with cell-based assays. These methods utilize glass slides, microtiter plates, and flow chamber to perform fluorescence analysis. These fluorescence detection methods, however, often incorporate expensive excitation light sources such as lasers or arc lamps for high intensity excitation. Typically, there is an excitation light source and a detection probe with an emission filter to pick up specific fluorescent signals. In an instrument such as fluorescent microscope, for example, a dichroic filter is required to reflect the light from the top normal (i.e., at a right angle) to the sample chamber. The emitted fluorescence is then picked up by passing through the dichroic filter into a detector such as a camera, spectrometer, etc. These fluorescence detection methods are also not used to directly measure sample concentration, since they do not measure samples in a specific fluid volume.

An example of a previous fluorescent cell counting technology is one that utilizes a filter cube (such as those provided by Omega Optical) in an assembly that includes optics, a camera, and a sample holder. Such as assembly may provide sufficient fluorescent images of cells and other biosamples for a number of applications, and it provides a simple and efficient method to generate fluorescent images of biological samples. This technology utilizes a fixed chamber volume, which is used to directly measure sample concentration, while analyzing fluorescence intensity. It, however, lacks the sensitivity for low fluorescent signal detection and imaging. One issue with such a system, for example, is that the excitation light may leak out into the emission filter in the filter cube. Another issue is that the filter cube format generally is inflexible in color selection. Only one specific filter cube and one LED could be used for one color. There is not much space in the instrument to incorporate other colors, making it difficult to allow multi-color applications.

Therefore, a long-felt need exists for cell counting systems and methods that provide capabilities for detection and imaging of low fluorescent signals such as that of surface markers on various types of cells.

SUMMARY OF THE INVENTION

The invention is based, in part, on the discovery of a unique design approach resulting in a much improved system for detecting and imaging (e.g., measuring, analyzing, counting, or monitoring) microscopic objects. The system includes an unconventional design for fluorescent excitation such that the system allows two or multiple oblique incident excitation beams. This novel approach significantly liberates the overall design of the system and enables multiple light sources to be placed with various incident angles.

To increase the capability for detection of low fluorescent signals, the background of the sample slides must be reduced and/or the fluorescent signal of the cells or biomolecules must be enhanced. The invention presented here describes a novel method for maximizing the fluorescent signal of the sample while minimizing the background noise of sample slides through the utilization of oblique excitation light sources and multiple LEDs (light-emitting diodes) illumination. Not only the new system paves the way for enhanced (i.e., more powerful) excitation by putting in place two or multiple excitation sources, it also enables flexible use of and selection for wavelengths and incident angles of the excitation beams. By allowing different combinations of angles of incident excitation beams, images may be generated that were not possible or could not be easily generated using prior systems.

In one aspect, the invention generally relates to a system for imaging microscopic objects. The system comprises: a sample chamber configured to hold a suspension of objects to be imaged in a sample, wherein the chamber comprising an optically clear window allowing exposure of the sample; at least one fluorescent light source capable of providing a fluorescent excitation light beam to the sample through the window; a bright-field light source capable of providing a bright-field light beam to the sample; and at least one light detection device for detecting a light signal from the sample thereby forming at least one image of the microscopic objects, wherein the fluorescent excitation light beam is at an incident angle other than normal to the window's plane of surface.

In certain preferred embodiments, the system comprises at least two fluorescent light sources that are capable of simultaneously providing two excitation light beams having the same (or different) wavelengths to the sample. In certain preferred embodiments, the system comprises multiple fluorescent light sources that are capable of simultaneously providing multiple excitation light beams having the same (or different) wavelengths to the sample.

In certain embodiments, the fluorescent excitation light beam(s) is at an incident angle of about 10° to about 80° (e.g., about 30° to about 70°, about 35° to about 55°, or less than about 45°, greater than about 45° and less than about 90°, or about 45°) in relation to the plane of surface of the sample chamber window.

The microscopic objects that may be imaged, monitored, analyzed, measured or counted include, but are not limited to, microbeads, bacteria, algae, fungi, mammalian cells, insect cells, plant cells, proteins, DNA molecules, and surface markers. In certain embodiments, the preferred microscopic objects include biomolecules and cells.

The sample chamber may have a fixed depth, ranging from about 1 μm to about 1,000 μm. In some preferred embodiments, the fixed depth ranges from about 1 μm to about 200 μm (e.g., from about 10 μm to about 100 μm). The covered sample chamber may be configured to hold a sample volume of about 1 μL to about 1,000 μL. In certain preferred embodiments, the covered sample chamber is configured to hold a sample volume of about 1 μL to about 500 μL (e.g., about 1 μL to about 100 μL). The fluorescent light sources may emit a beam having a wavelength ranging from about 300 nm to about 10,000 nm (e.g., from about 300 nm to about 2,000 nm or from about 300 nm to about 1,000 nm).

In another aspect, the invention generally relates to a system for counting cells or biomolecules. The system comprises: a covered chamber configured to hold a suspension of cells or biomolecules in a sample, wherein the chamber comprising an optically clear window allowing exposure of the sample; two or more fluorescent light sources, each being capable of independently providing a fluorescent excitation light beam to the sample through the window, wherein each fluorescent excitation light beam is at an incident angle other than normal to the window's plane of surface; a bright-field light source capable of providing a bright-field light beam to the sample; at least one light detection device for detecting a light signal from the sample; and a shutter for controlling passage of the bright-field light beam to the sample.

In yet another aspect, the invention generally relates to a method for measuring a characteristic of a biological sample. The method comprises: acquiring at least one static bright-field image of the biological sample by directing a bright-field light beam to the sample; acquiring at least one static fluorescent image of the biological sample by directing an excitation light beam to the sample; and comparing the at least one bright-field image to the at least one fluorescent image to determine the characteristic of the biological sample, wherein the excitation light beam is at an oblique angle to the bright-field light beam.

In certain preferred embodiments, the fluorescent image is acquired from excitation by directing at least two excitation light beams to the sample. In certain other preferred embodiments, the fluorescent image is acquired from excitation by directing multiple (e.g., three, four) excitation light beams to the sample.

In yet another aspect, the invention generally relates to a method for detecting a biomolecule in a sample. The method comprises: acquiring at least one static bright-field image of the biological sample by directing a bright-field light beam to the sample; acquiring at least static fluorescent image of the biological sample by directing an excitation light beam to the sample; and comparing the at least one bright-field image to the at least one fluorescent image to determine the characteristic of the biological sample, wherein the excitation light beam is at an oblique angle to the bright-field light beam.

In yet another aspect, the invention generally relates to a method for determining a concentration or number count of a certain type of cells in a population of cells in a sample. The method comprises: contacting a sample comprising cells with a fluorescently labeled agent that specifically binds the certain type of cells in the sample; loading the sample into a covered chamber having a known height, wherein the population of cells is suspended within the chamber; acquiring at least one static bright-field image of the population of cells in the sample; acquiring at least one static fluorescent image of the population of cells in the sample; and comparing cell count from the bright-field image to cell count from the fluorescent image to determine the concentration or number count of the certain type of cells in the population of cells, wherein the excitation light beam is at an oblique angle to the bright-field light beam.

BRIEF DESCRIPTION OF THE DRAWINGS

FIG. 4 an exemplary depiction of an embodiment of the system disclosed herein.

DETAILED DESCRIPTION OF THE INVENTION

Figure 1:
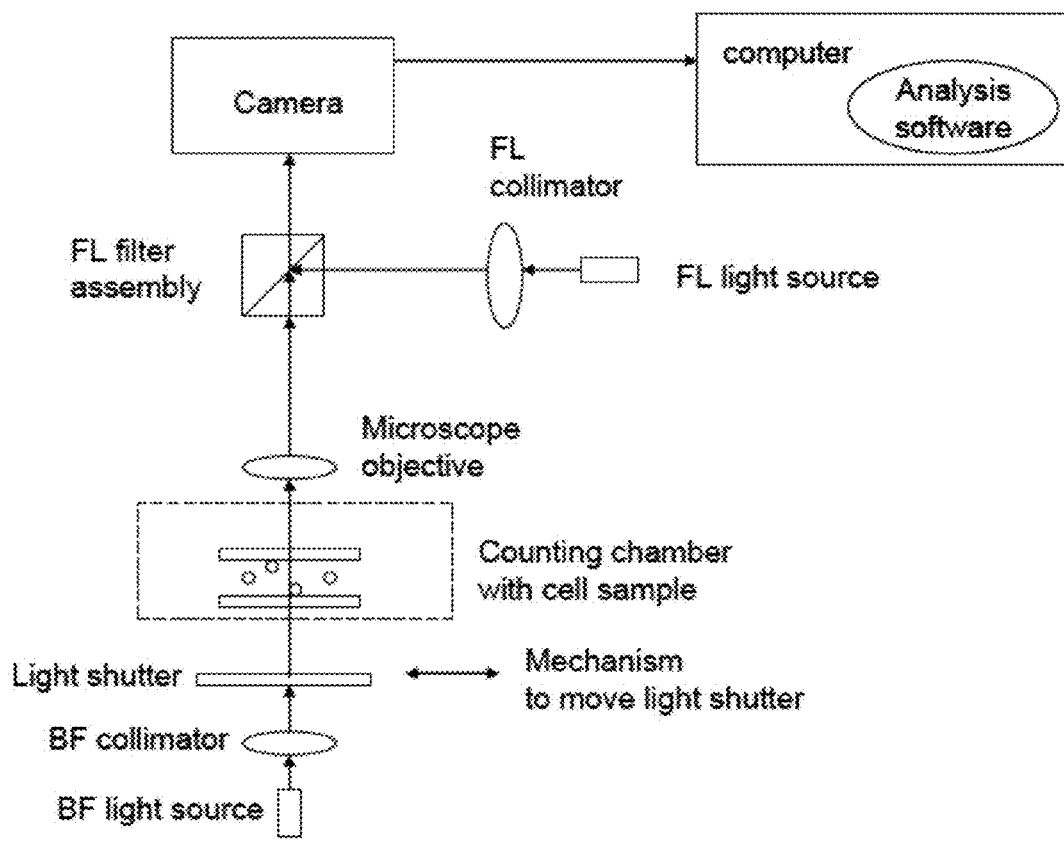
FIG. 1 an exemplary prior art cell counting system.

The invention relates to systems and methods for detecting and imaging microscopic particles such as cells and biological molecules. The invention is based, in part, on the discovery of a unique design that enables in a much improved system for detecting and imaging (e.g., measuring, analyzing, counting or monitoring) microscopic objects in solution samples. The system includes an unconventional approach to fluorescent excitation such that it allows two or multiple oblique incident excitation beams that are simultaneously operatable. This novel approach significantly revolutionizes and liberates the overall design of an imaging system and enables multiple (same or different) light sources to be placed with various incident angles to the sample. The new system thus paves the way for enhanced excitation power by putting in place two or multiple excitation sources. It additionally allows the flexible use of and selection of wavelengths and incident angles of excitation beams. With different and combinations of angles of incident excitation beams, one can detect and generate images that were not possible or easily generated using prior systems.

The biological mechanisms of many diseases have been clarified by microscopic examination of tissue samples or body fluids. Histopathological examination has also permitted the development of effective medical treatments for a variety of illnesses. In standard anatomical pathology, a diagnosis is made on the basis of cell morphology and staining characteristics. Microscopic examination and classification of tissue samples stained by standard methods (such as hematoxylin and eosin) has improved cancer treatment significantly. Tumor samples, for example, can be examined to characterize the tumor type and suggest whether the patient will respond to a particular form of chemotherapy.

Recent advances in molecular medicine have provided an even greater opportunity to understand the cellular mechanisms of disease, and select appropriate treatments with the greatest likelihood of success. For example, certain hormone dependent breast tumor cells have an increased expression of estrogen receptors indicating that the patient from whom the tumor was taken will likely respond to certain anti-estrogen drug treatments. Other diagnostic and prognostic cellular changes include the presence of tumor specific cell surface antigens (as in melanoma), the production of embryonic proteins (such as carcinoembryonic glycoprotein antigen produced by gastrointestinal tumors), and genetic abnormalities (such as activated oncogenes in tumors). A variety of techniques have evolved to detect the presence of these cellular abnormalities, including immunophenotyping with monoclonal antibodies, in situ hybridization using nucleic acid probes, and DNA amplification using the polymerase chain reaction (PCR).

Effective use of such biomarkers in assisting in the diagnosis and identification of an effective therapeutic regimen has been impeded by the inability of current automated analysis systems to utilize and identify the varied biomarkers in a cost efficient, time sensitive, and reproducible manner. Previous techniques and systems have often proven inadequate for the efficient analysis of tissue samples that require a rapid parallel analysis of a variety of independent microscopic, histologic and/or molecular characteristics.

Furthermore, manual methods can be extremely time consuming and often require a high degree of professional training and quality control to identify and/or quantify cells. This is not only true for tumor cell identification and detection, but also for other applications ranging from neutrophil alkaline phosphatase assays, reticulocyte counting and maturation assessment, etc. The associated manual labor leads to a high cost for these procedures in addition to the potential errors that can arise from long, laborious manual examinations.

One fluorescent cell counting technology has utilized a filter cube in an assembly with optics, camera, and sample holder. In certain applications, it was able to provide sufficient fluorescent images of cells and other biosamples. Although the technology provides a simple and efficient method to generate fluorescent images of biological samples, it lacks the sensitivity needed for low fluorescent signal detection and imaging. Excitation light leakage and system design and color selection inflexibility (due to the filter cube form a) are among the key shortcomings. Only one specific filter cube and one LED could be used for one color. Not much additional space is available to incorporate other colors. (Exemplary counting systems and related methods may be found in PCT/US09/39863 & U.S. Patent Pub. No. 2004/0145805.)

Depicted in FIG. 1 is an example of a prior art cell-counting system. The system includes a counting chamber, a fluorescent light source (connected to a fluorescent light beam narrowing device), and a bright-field light source (connected to a bright-field light beam narrowing device). The cell counting system in FIG. 1 further includes a detection device (camera), and a fluorescent filter assembly that allows excitation light from the fluorescent light source to illuminate the sample in the chamber. In FIG. 1, the fluorescent excitation light shines on the sample in the counting chamber at a right (normal) angle.

The present invention significantly improves the sensitivity and detection limit of the above-system, at least in two major aspects. First, an oblique incidence excitation light source is used to minimize the background signal due to light leakage from excitation filter to emission filter that is common in a filter cube method. Second, by applying the oblique excitation concept, multiple LEDs can be easily incorporated into an instrument to illuminate the samples, thereby increasing the fluorescent signal from a sample and reducing the exposure time needed to acquire an image in a filter cube system (thus making the new system comparable to a laser or arc lamp excitation).

Figure 2:
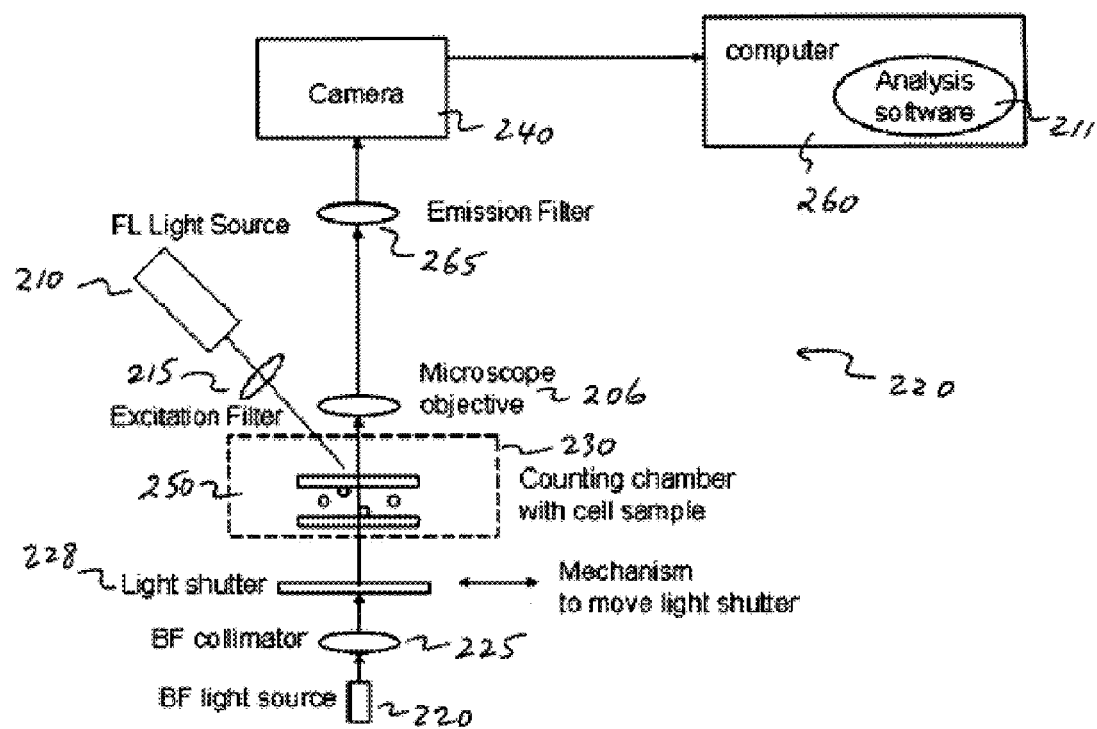
FIG. 2 an exemplary system according to the present invention.

Referring to FIG. 2, which is a schematic diagram of an exemplary embodiment of a cell counting system according to the present invention. The cell counting system 200 includes a fluorescent light source 210 connected to a fluorescent light beam narrowing device 215, a bright-field light source 220 connected to a bright-field light beam narrowing device 225. The cell counting system further includes a counting chamber 230 and a detection device 240 (camera). In this system, the fluorescent excitation light shines on the sample 250 in the counting chamber 230 at an oblique angle. The cell counting system 200 further includes a microscope objective 206 and a movable light shutter 228. The detection device can be a camera, such as a CCD (charge-coupled device) camera, for acquiring images. The camera may be fitted with a cooling capability. In certain embodiments, microscope objective movements are under the control of a computer 260 operably connected to the system 200.

The counting chamber 230 has a known height that may be pre-selected, adjusted, or fixed. The counting chamber 230 is covered or otherwise closed such that the suspension of sample therein would not lose volume due to evaporation. The chamber 230 is loaded with a sample by pipetting the sample into the sample introduction port of the chamber 230. As the sample is loaded into the chamber, air escapes the chamber 230 through the air escape port in the chamber 230. An exemplary sample size is 20 µl although actual sample size may vary according to the application and instrument setup. Once the chamber 230 is loaded with the sample, the chamber 230 is loaded into the counting system 200 through a slot in a housing of the system. The fluorescent light source and the bright-field light source can be a light emitting diode. The fluorescent light beam narrowing device and the bright-field light beam narrowing device can be collimators.

Once an image is taken, the sample volume under interrogation can be obtained from the height of the counting chamber and the area of the sample that is imaged. The interrogated sample volume can be obtained and is known for each image taken. It should be noted that the chamber height may be varied from application to application as long as the interrogated sample volume can be obtained or is known.

System 200 is configured for bright-field imaging and fluorescent imaging of the sample in the chamber 230. The components of the cell counting system 200 are encased in a housing. The bright-field light source 220 is positioned at the base of the housing and is configured to emit light onto the sample in the chamber 230 positioned in-line above the bright-field light source 220. Between the chamber 230 and the bright-field light source 220 is a bright-field light beam narrowing device 225. The beam narrowing device focuses the light emitted from the bright-field light source 220, and directs the light onto the sample in the chamber 230. Also positioned between the chamber 230 and the bright-field light source 220 is a movable light shutter 228. The movable light shutter 228 is located above the bright-field light beam narrowing device 225 and below the chamber 230. The light shutter 228 is connected to a mechanism for moving the shutter, such as a motor or a solenoid. The light shutter 228 is mechanically moved out of line with the bright-field light source 220 to allow the light from the bright-field light source 220 to interact with the sample in the chamber 230 during bright-field imaging. The light shutter 228 is mechanically moved in-line with the bright-field light source 220 to block the light from the bright-field light source 220 from interacting with the sample in the chamber 230 during fluorescent imaging.

After the light beam from the bright-field light source 220 passes through the sample in the chamber 230, the light subsequently passes through a microscope objective 206. The microscope objective 206 is responsible for primary image formation and is involved in determining quality of images that the system 200 is capable of producing. Microscope objective 206 is also involved in determining the magnification of a particular sample and the resolution under which fine sample details may be observed in the system 200. Microscope objectives are commercially available from Olympus America Inc. (Center Valley, Pa.).

After the light from the bright-field light source 220 passes through the microscope objective 206, the emitted light from the sample passes through an emission filter 265, and the emitted light from the sample in the chamber 230 is acquired by the detection device 240. The emission filter 265 is in-line with the bright-field light source 220, the bright-field beam narrowing device 225, the chamber 230, the microscope objective 206, and the detection device 240. An exemplary detection device is a CCD camera commercially available from Olympus America Inc. (Center Valley, Pa.). The image from the detection device 240 is transmitted to a computer 260 having analysis software 211.

As shown in FIG. 2, the system includes at least one fluorescent light source 210 for fluorescent imaging of the sample in the chamber 230. The fluorescent light source 210 emits excitation light through a fluorescent beam narrowing device 215.

During fluorescent detection, the light shutter 228 is mechanically moved in-line with the bright-field light source 220 to block the white light from the bright-field light source 220 from interacting with the sample in the chamber 230 during fluorescent imaging.

Figure 3:
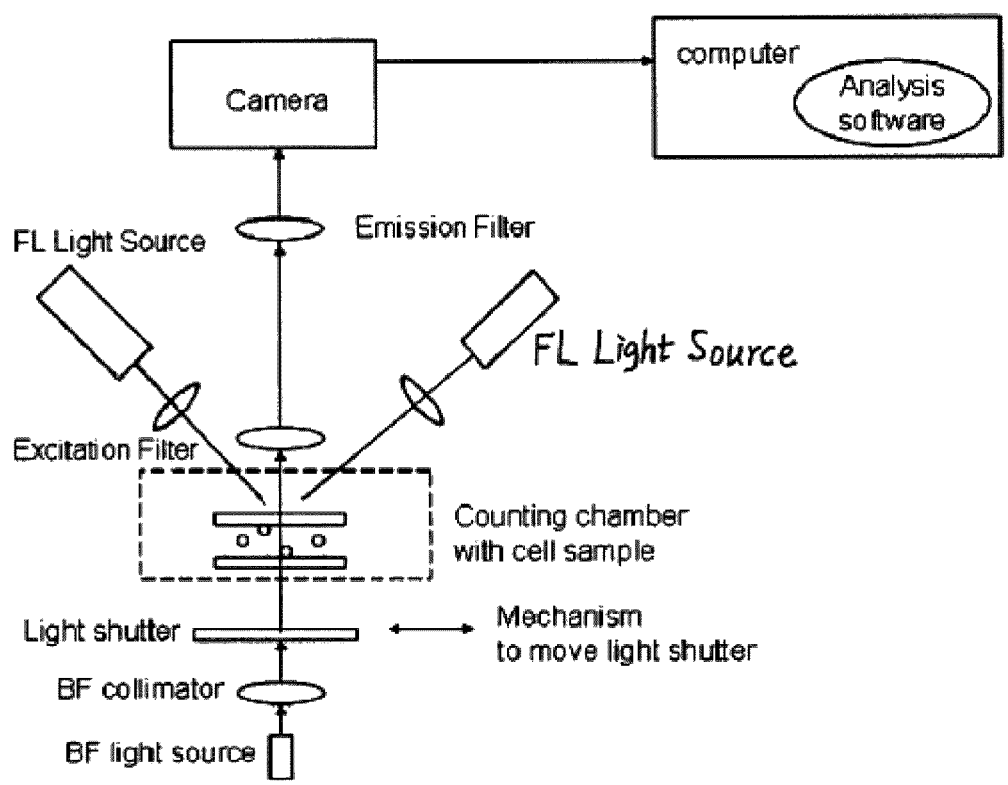
FIG. 3 an exemplary depiction of an embodiment of the system disclosed herein.

FIG. 2 shows one set of fluorescent light source and fluorescent beam narrowing device. Two or multiple sets of fluorescent light sources and fluorescent beam narrowing devices may be used for fluorescence excitation and emission detection. FIG. 3 illustrates such a system with two sets of fluorescent excitation light sources. With two or multiple (e.g., 3 or 4) sets of fluorescence excitation and emission available on the same sample, variable and/or stronger excitations may be achieved, as well as more than one fluorescent label may be used for advanced assays. FIGS. 4A and 4B are pictures showing different views of an exemplary cell counting system.

Thus, the cell counting system of the invention includes an unconventional design for fluorescent excitation such that the system allows two or multiple oblique incident excitation beams. This novel approach significantly liberates the overall design of the system and enables multiple light sources to be placed with various incident angles. The cell counting system described herein captures bright-field and fluorescent images of cells or biomolecules in the chamber, analyzes the number of cells or biomolecules, sizes and fluorescent intensity of each cell, and then converts this data to concentration, size and fluorescence histograms and scatter plots. The cell counting system of the invention is useful for various biological assays and other applications.

In one aspect, the invention generally relates to a system for imaging microscopic objects. The system comprises: a sample chamber configured to hold a suspension of objects to be imaged in a sample, wherein the chamber comprising an optically clear window allowing exposure of the sample; at least one fluorescent light source capable of providing a fluorescent excitation light beam to the sample through the window; a bright-field light source capable of providing a bright-field light beam to the sample; and at least one light detection device for detecting a light signal from the sample thereby forming at least one image of the microscopic objects, wherein the fluorescent excitation light beam is at an incident angle other than normal to the window's plane of surface.

In certain preferred embodiments, the system comprises at least two fluorescent light sources that are capable of simultaneously providing two excitation light beams having the same (or different) wavelengths to the sample. In certain preferred embodiments, the system comprises multiple fluorescent light sources that are capable of simultaneously providing multiple excitation light beams having the same (or different) wavelengths to the sample.

In certain embodiments, the fluorescent excitation light beam(s) is at an incident angle of about 10° to about 80° (e.g., about 30° to about 70°, about 35° to about 55°, or less than about 45°, greater than about 45° and less than about 90°, or about 45°) in relation to the plane of surface of the sample chamber window.

In certain embodiments, the two or multiple fluorescent excitation light beams have the same incident angle in relation to the window's plane of surface. In certain embodiments, the two or multiple fluorescent excitation light beams have a combination of different incident angles in relation to the window's plane of surface.

In certain embodiments, the two or multiple fluorescent excitation light beams have different wavelengths. In certain embodiments, the two or multiple fluorescent excitation light beams have the same wavelengths. The excitation light source may have selectable excitation wavelengths.

The microscopic objects that may be imaged, monitored, analyzed, measured or counted include, but are not limited to, microbeads, bacteria, algae, fungi, mammalian cells, insect cells, plant cells, proteins, DNA molecules, and surface markers. In certain embodiments, the preferred microscopic objects include biomolecules and cells.

In some preferred embodiments, the sample chamber is covered (or closed).

The sample chamber may have a fixed depth, ranging from about 1 µm to about 1,000 µm. In some preferred embodiments, the fixed depth ranges from about 1 µm to about 200 µm (e.g., from about 10 µm to about 100 µm).

The covered sample chamber may be configured to hold a sample volume of about 1 µL to about 1,000 µL. In certain preferred embodiments, the covered sample chamber is configured to hold a sample volume of about 1 µL to about 500 µL (e.g., about 1 µL to about 100 µL).

The fluorescent light sources may emit a beam having a wavelength ranging from about 300 nm to about 10,000 nm (e.g., from about 300 nm to about 2,000 nm or from about 300 nm to about 1,000 nm).

In another aspect, the invention generally relates to a system for counting cells or biomolecules. The system comprises: a covered chamber configured to hold a suspension of cells or biomolecules in a sample, wherein the chamber comprising an optically clear window allowing exposure of the sample; two or more fluorescent light sources, each being capable of independently providing a fluorescent excitation light beam to the sample through the window, wherein each fluorescent excitation light beam is at an incident angle other than normal to the window's plane of surface; a bright-field light source capable of providing a bright-field light beam to the sample; at least one light detection device for detecting a light signal from the sample; and a shutter for controlling passage of the bright-field light beam to the sample.

In yet another aspect, the invention generally relates to a method for measuring a characteristic of a biological sample. The method comprises: acquiring at least one static bright-field image of the biological sample by directing a bright-field light beam to the sample; acquiring at least one static fluorescent image of the biological sample by directing an excitation light beam to the sample; and comparing the at least one bright-field image to the at least one fluorescent image to determine the characteristic of the biological sample, wherein the excitation light beam is at an oblique angle to the bright-field light beam.

In certain preferred embodiments, the fluorescent image is acquired from excitation by directing at least two excitation light beams to the sample.

In certain other preferred embodiments, the fluorescent image is acquired from excitation by directing multiple (e.g., three, four) excitation light beams to the sample.

Each of the excitation light beams may have the same (or different) oblique angle to the bright-field light beam.

The excitation light sources may emit lights ranging from about 300 nm to about 10,000 nm (e.g., from about 300 nm to about 2,000 nm or from about 300 nm to about 1,000 nm).

In yet another aspect, the invention generally relates to a method for detecting a biomolecule in a sample. The method comprises: acquiring at least one static bright-field image of the biological sample by directing a bright-field light beam to the sample; acquiring at least static fluorescent image of the biological sample by directing an excitation light beam to the sample; and comparing the at least one bright-field image to the at least one fluorescent image to determine the characteristic of the biological sample, wherein the excitation light beam is at an oblique angle to the bright-field light beam.

In certain embodiments, the excitation light beams are at about 45° angle to the bright-field light beam. In certain embodiments, the excitation light beams are less than about 45° angle to the bright-field light beam. In certain embodiments, the excitation light beams are greater than about 45° angle to the bright-field light beam.

In yet another aspect, the invention generally relates to a method for determining a concentration or number count of a certain type of cells in a population of cells in a sample. The method comprises: contacting a sample comprising cells with a fluorescently labeled agent that specifically binds the certain type of cells in the sample; loading the sample into a covered chamber having a known height, wherein the population of cells is suspended within the chamber; acquiring at least one static bright-field image of the population of cells in the sample; acquiring at least one static fluorescent image of the population of cells in the sample; and comparing cell count from the bright-field image to cell count from the fluorescent image to determine the concentration or number count of the certain type of cells in the population of cells, wherein the excitation light beam is at an oblique angle to the bright-field light beam.

The invention has at least two unique advantages over the previous design. The first advantage is the flexibility for multi-emission incorporation, which utilizes multiple LEDs and multiple filters to perform multi-color fluorescence detection. The second unique advantage is the reduction of background caused the light leaking from excitation to the emission filter. Furthermore, since the excitation light is at an oblique incidence, less scattered light reflects back through the objective, thereby further reducing the background.

Samples that may be analyzed using the methods of the invention include biological materials obtained from or derived from living organisms. Typically the sample will include cells, tissue, or biomolecules, such as proteins, polynucleotides (e.g., DNA or RNA), organic material, and any combination of the foregoing. Such samples include, but are not limited to, hair, skin, tissue, cultured cells, cultured cell media, and body fluids.

A tissue is a mass of connected cells and/or extracellular matrix material, e.g., CNS tissue, neural tissue, eye tissue, liver tissue, placental tissue, mammary gland tissue, gastrointestinal tissue, musculoskeletal tissue, genitourinary tissue, and the like, derived from, for example, a human or other mammal and includes the connecting material and the liquid material in association with the cells and/or tissues. A body fluid is a liquid material derived from, for example, a human or other mammal. Such body fluids include, but are not limited to, blood, plasma, serum, serum derivatives, bile, phlegm, saliva, sweat, amniotic fluid, mammary fluid, and cerebrospinal fluid (CSF), such as lumbar or ventricular CSF. A sample also may be media containing cells or biological material.

Systems of the invention can also be used to interrogate cell lines. Cell lines refer to specific cells that can grow indefinitely given the appropriate medium and conditions. Systmes of the invention can be used to interrogate any type of cell line. Cell lines can be mammalian cell lines, insect cell lines or plant cell lines. Exemplary cell lines can include tumor cell lines or stem cell lines.

EXAMPLES

The instrument was set up using a Lumenera Vision camera and standard Thor lab parts (FIG. 2). The camera sits on top with a 160 mm lens tube and a standard DIN objective with an emission filter directly above the objective lens. The fluorescent excitation light source sits at about 42° above the sample stage, with the center of the beam illuminating the sample area. Multiple LEDs were set up surrounding the sample stage simultaneously.

Sample Preparation

UV fluorescent beads (LinearFlow, Invitrogen) at 100 and 0.8% were used to test the feasibility of the instrumental setup. In addition, non fluorescent beads were also tested for nonspecific signals. UV, blue, green, and red fluorescent beads (LinearFlow, Invitrogen) at 100% were mixed and used to test the feasibility of the multi-emission instrumental setup. The images obtained (FIG. 5) were overlaid using Adobe Photoshop.

Background Signal Reduction

Figure 6:
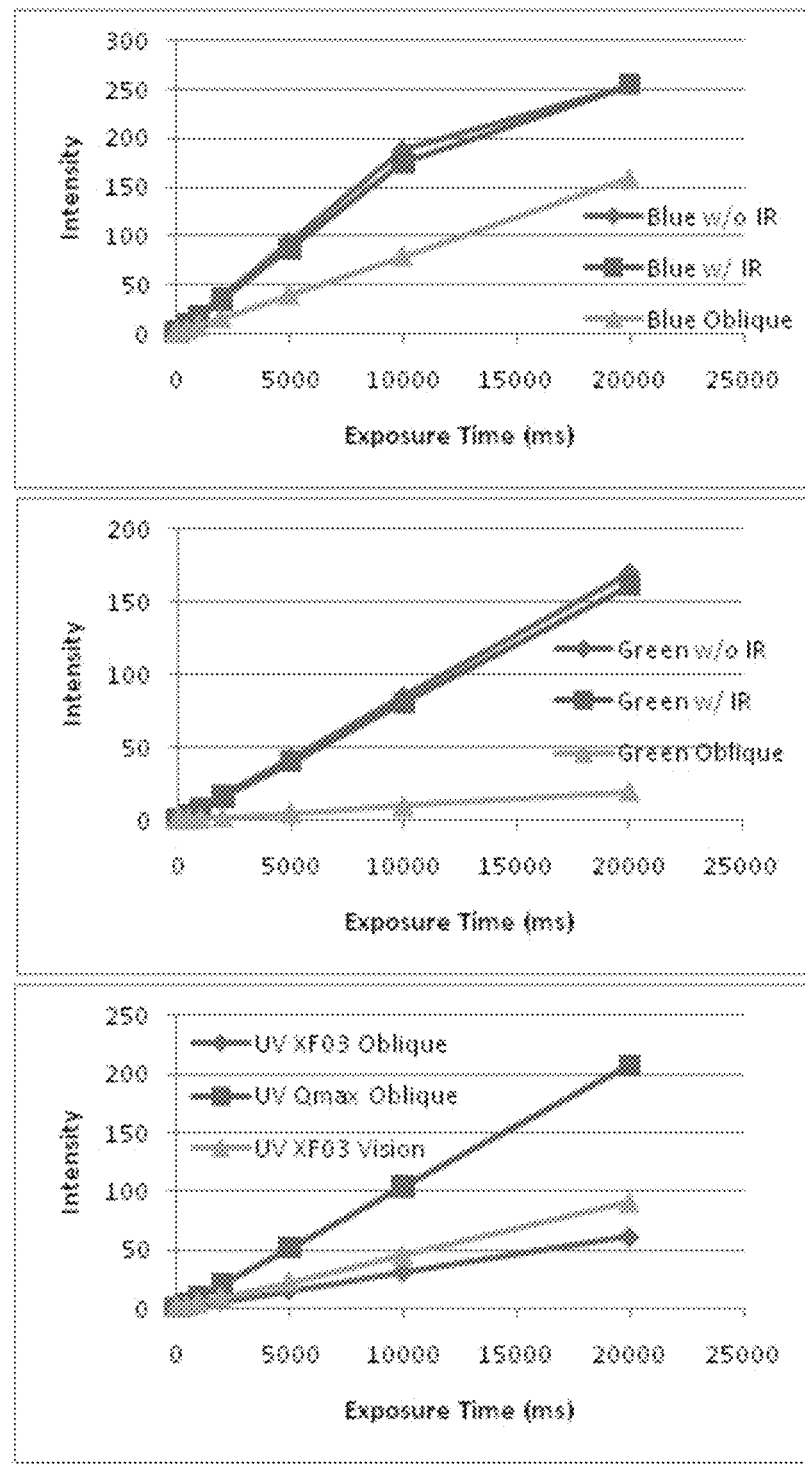
FIG. 6 an exemplary of background intensity reduction of oblique incidence setup.

Images were taken using blue, green, and UV LEDs at oblique incidence using a simple Nexcelom counting slide and no samples to measure the background effect of this method. The images were taken at various exposure times and with different LEDs to compare to the filter cube method (FIG. 6).

Multiple LEDS Signal Enhancement

Figure 7:
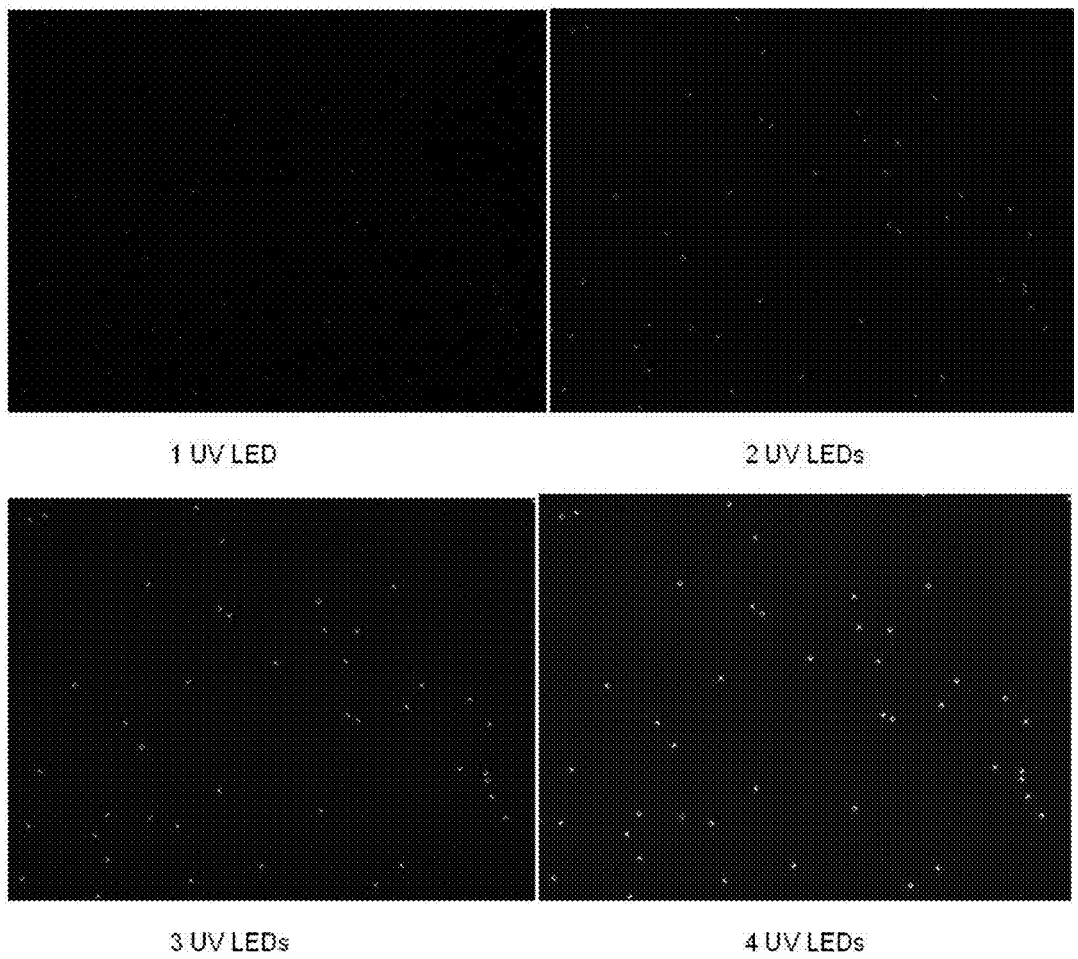
FIG. 7 an exemplary of images of LinearFlow UV fluorescent beads excited with multiple LEDs with the same wavelength at oblique incidence.
Figure 8:
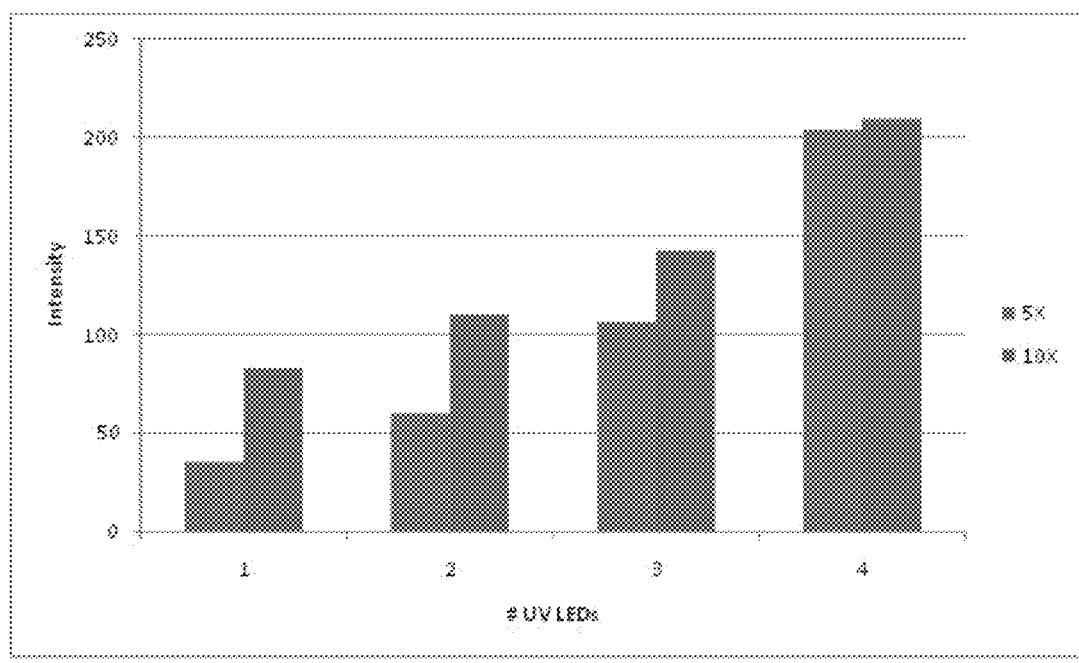
FIG. 8 an exemplary excitation light enhancement utilizing multiple LEDs at the same wavelength for 5× objective.
Figure 9:
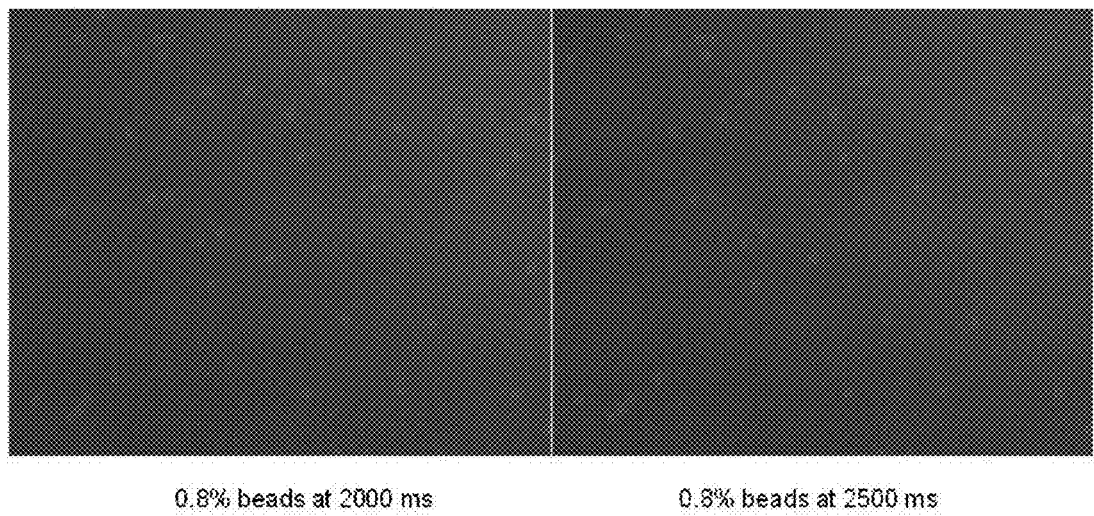
FIG. 9 an exemplary of sensitivity enhancement, where 0.8% fluorescent intensity beads were able to be imaged using oblique incidence setup.
Figure 10:
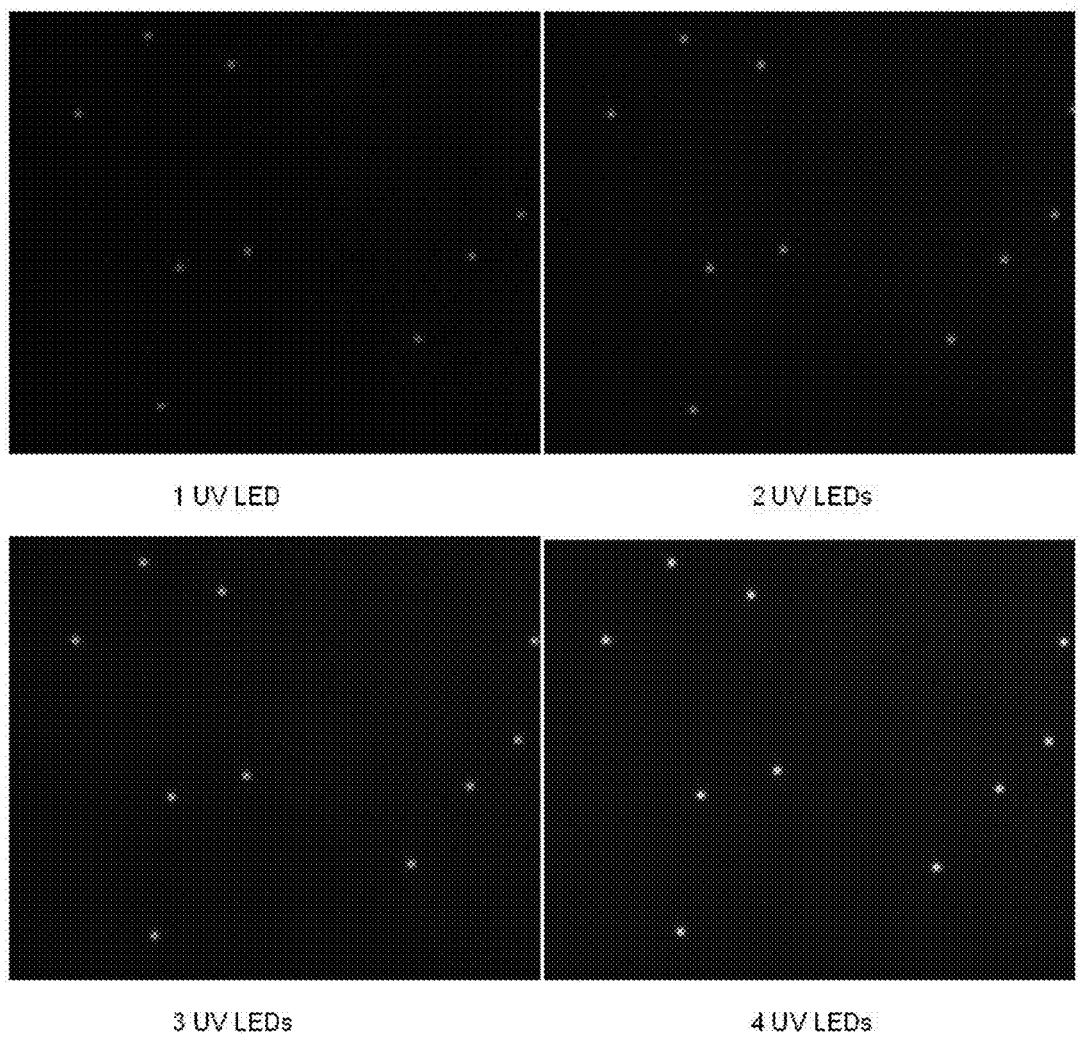
FIG. 10 an exemplary excitation light enhancement utilizing multiple LEDs at the same wavelength for 10× objective.

Signal enhancement was compared by utilizing 1 to 4 LEDs and measuring the bead signals (FIGS. 7, 8, 10). These were performed with high intensity beads and low intensity beads, where the lowest percent fluorescent beads at 0.8% were able to be imaged FIG. 9.

Multi-emission Setup

Figure 5:
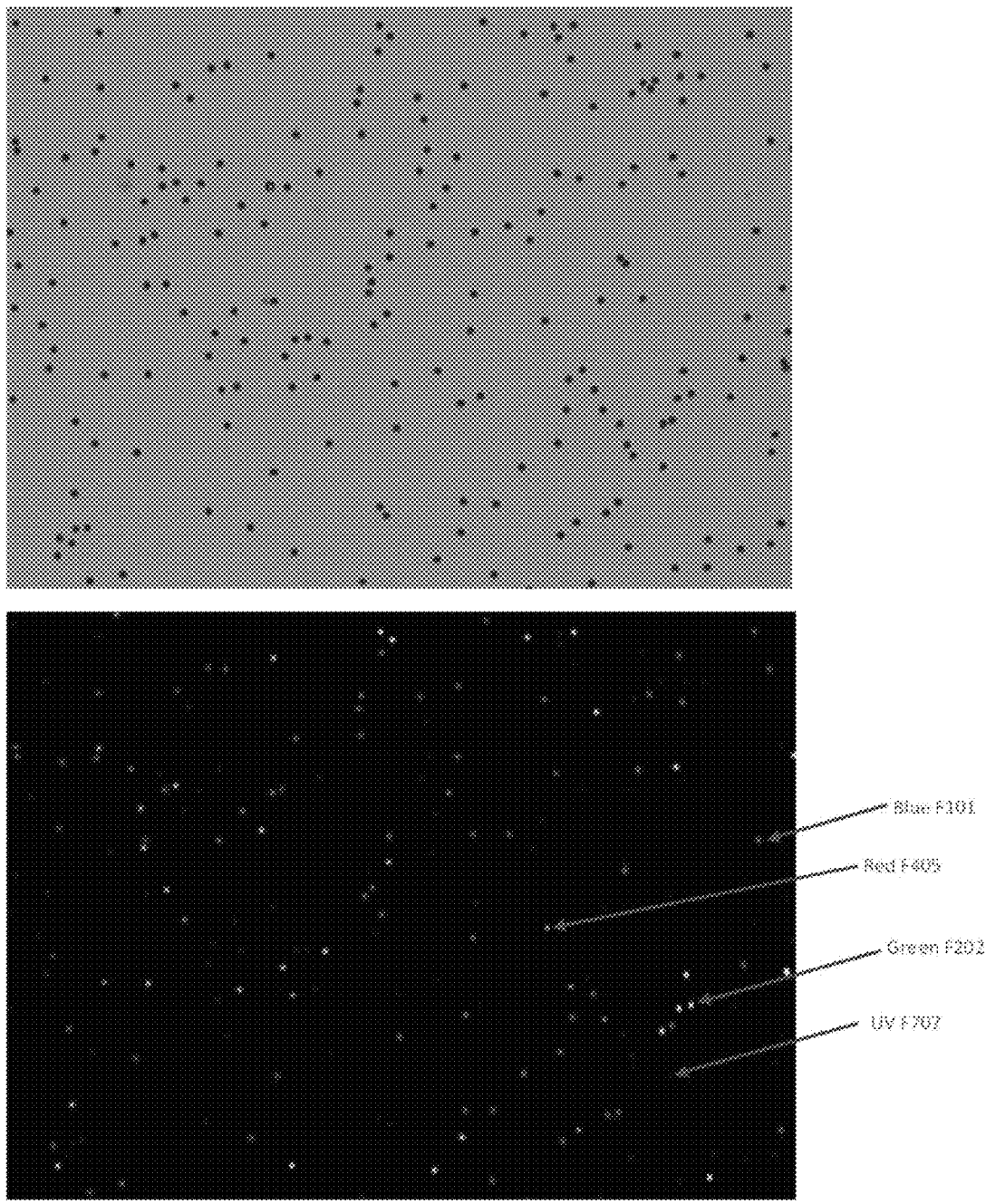
FIG. 5 an exemplary of an image of fluorescent emission of LinearFlow beads (Invitrogen) excited with multiple LEDs with different wavelengths at oblique incidence.

By utilizing the oblique incident illumination method, multi-emission of fluorescence is enabled. In FIG. 5, four images were taken using each color and merged using Adobe Photoshop. A clear match is observed between the bright field and the fluorescent image: four different types of beads were observed, which confirmed the use of the setup in multiplexed fluorescent detection.

Background Signal Reduction

By using the oblique method, the background was significantly reduced for blue, green, and UV LEDs. In FIG. 6, the background reduction for blue, green, and UV LEDs were approximately 2, 8, and 3 times, respectively. Thus, the detection limit was significantly improved (allowing lower fluorescence for various excitation sources or fluorophores).

The background reductions for blue, green, and UV LEDs were 2, 8, and 3 times respectively. In addition, the signal enhancement relates to the number of LEDs linearly; therefore, where 4 LEDs are used, there are four times of enhancement. Signal to Noise ratio (S/N), N'=N/2, 8, or 3 and S'=4 for 4 LEDs gave final S/N enhancement would be 8, 32, and 12 times for blue, green, and UV LEDs.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance which can be adapted to the practice of this invention in its various embodiments and equivalents thereof.

What is claimed is:

1. A system for imaging microscopic objects, comprising:
   a covered sample chamber having a fixed depth ranging from about 1 µm to about 200 µm, the covered sample chamber being configured to hold about 1 µL to about 1,000 µL of a liquid suspension of microscopic objects to be imaged in a liquid sample, wherein the covered sample chamber comprising an optically clear window allowing exposure of the liquid sample;
   at least one fluorescent light source capable of providing a fluorescent excitation light beam to the liquid sample through the window;
   a bright-field light source capable of providing a bright-field light beam to the liquid sample; and
   at least one light detection device for detecting a light signal from the liquid sample thereby forming at least one image of the microscopic objects,
   wherein the fluorescent excitation light beam is at an oblique angle to the bright-field light beam and is oblique to the window's plane of surface, and
   the fluorescent excitation light beam comprises a wavelength ranging from about 300 nm to about 10,000 nm.

2. The system of claim 1, wherein the system comprises at least two fluorescent light sources capable of simultaneously providing two excitation light beams having the same or different wavelengths to the sample.

3. The system of claim 2, wherein the system comprises four fluorescent light sources capable of simultaneously providing four excitation light beams having the same or different wavelengths to the sample.

4. The system of claim 2, wherein the at least two fluorescent excitation light beams have different incident angles in relation to the window's plane of surface.

5. The system of claim 2, having multiple fluorescent excitation light beams having the same incident angles in relation to the window's plane of surface.

6. The system of claim 2, having multiple fluorescent excitation light beams having different incident angles in relation to the window's plane of surface.

7. The system of claim 1, wherein the fluorescent excitation light beam is at an incident angle of about 10° to about 80° in relation to the window's plane of surface.

8. The system of claim 1, wherein the fluorescent excitation light beam is at an incident angle of about 45° in relation to the window's plane of surface.

9. The system of claim 1, wherein the microscopic objects are selected from microbeads, bacteria, algae, fungi, mammalian cells, insect cells, plant cells, proteins, DNA molecules, and surface markers.

10. The system of claim 9, wherein the microscopic objects are selected from the group consisting of protein surface markers, weak fluorescence labels, and DNA molecules.

11. The system of claim 1, wherein the microscopic objects comprise biomolecules.

12. The system of claim 1, wherein the fixed depth ranges from about 10 µm to about 100 µm.

13. A system for counting cells or biomolecules, comprising:
   a covered sample chamber configured to hold a liquid suspension of cells or biomolecules in a liquid sample, wherein the sample chamber comprising an optically clear window allowing exposure of the liquid sample;
   two or more fluorescent light sources, each being capable of independently providing a fluorescent excitation light beam to the liquid sample through the window, wherein each fluorescent excitation light beam is at an incident angle other than normal to the window's plane of surface;
   a bright-field light source capable of providing a bright-field light beam to the liquid sample;
   at least one light detection device for detecting a light signal from the liquid sample; and
   a shutter for controlling passage of the bright-field light beam to the liquid sample.

14. A method for detecting a biomolecule in a liquid biological sample comprising:
   acquiring at least one static bright-field image of the biological sample by directing a bright-field light beam to the sample;
   acquiring at least one static fluorescent image of the biological sample by directing at least two excitation light beams to the sample; and
   comparing the at least one bright-field image to the at least one fluorescent image to detect the biomolecule in the biological sample,
   wherein each of at least two the excitation light beams is at an oblique angle to the bright-field light beam.

15. A method for determining a concentration or number count of a type of cells in a population of cells in a liquid sample, comprising:
   contacting a liquid sample comprising a suspension of cells with a fluorescently labeled agent that specifically binds the certain type of cells in the liquid sample;
   loading the sample into a covered chamber having a known height, wherein the population of cells is suspended within the chamber;
   acquiring at least one static bright-field image of the population of cells in the liquid sample;
   acquiring at least one static fluorescent image of the population of cells in the liquid sample; and comparing cell count from the bright-field image to cell count from the fluorescent image to determine the concentration or number count of the certain type of cells in the population of cells,
wherein the excitation light beam is at an oblique angle to the bright-field light beam.

\* \* \* \* \*

(12) EX PARTE REEXAMINATION CERTIFICATE (11729th)
United States Patent
Chan et al.

(10) Number: US 9,329,130 C1
(45) Certificate Issued: Sep. 17, 2020

(54) SYSTEMS AND METHODS FOR COUNTING CELLS AND BIOMOLECULES

(75) Inventors: Leo L. Chan, North Andover, MA (US); Peter Li, North Andover, MA (US)

(73) Assignee: NEXCELOM BIOSCIENCE LLC, Lawrence, MA (US)

Reexamination Request:
No. 90/014,284, Apr. 11, 2019

Reexamination Certificate for:
Patent No.: 9,329,130
Issued: May 3, 2016
Appl. No.: 13/519,282
PCT Filed: Jan. 11, 2011
PCT No.: PCT/US2011/020766
§ 371 (c)(1),
(2), (4) Date: Jan. 3, 2013
PCT Pub. No.: WO2011/088014
PCT Pub. Date: Jul. 21, 2011

Related U.S. Application Data

(60) Provisional application No. 61/294,236, filed on Jan. 12, 2010.

(51) Int. Cl.
| | |
|---|---|
| G01J 3/10 | (2006.01) |
| G01J 3/44 | (2006.01) |
| G01N 15/14 | (2006.01) |
| G01N 21/64 | (2006.01) |
| G01N 33/50 | (2006.01) |
| G01J 5/10 | (2006.01) |
| G01N 21/3581 | (2014.01) |
| G01N 21/17 | (2006.01) |

(52) U.S. Cl.
CPC .............. *G01J 3/10* (2013.01); *G01J 3/4406* (2013.01); *G01J 5/10* (2013.01); *G01N 15/1463* (2013.01); *G01N 21/3581* (2013.01); *G01N 21/64* (2013.01); *G01N 21/6428* (2013.01); *G01N 21/6456* (2013.01); *G01N 21/6458* (2013.01); *G01N 21/6486* (2013.01); *G01N 33/5005* (2013.01); *G01N 2015/1486* (2013.01); *G01N 2021/174* (2013.01); *G01N 2021/1736* (2013.01); *G01N 2021/6419* (2013.01); *G01N 2021/6441* (2013.01); *G01N 2021/6491* (2013.01); *G01N 2201/0627* (2013.01)

(58) Field of Classification Search
CPC .......... G01N 15/1463; G01N 21/6456; G01N 33/5005; G01N 21/6486; G01N 21/6458; G01N 21/6428; G01N 2201/0627; G01N 15/1486; G01N 21/3581; G01N 21/64; G01N 2021/174; G01N 2021/6441; G01N 2021/6491; G01J 3/10; G01J 5/10
See application file for complete search history.

(56) References Cited

To view the complete listing of prior art documents cited during the proceeding for Reexamination Control Number 90/014,284, please refer to the USPTO's public Patent Application Information Retrieval (PAIR) system under the Display References tab.

*Primary Examiner* — Albert J Gagliardi

(57) ABSTRACT

The invention generally relates to analytical and monitoring systems useful for analyzing and measuring cells and biological samples. More particularly, the invention relates to systems and methods for imaging, measuring, counting, analyzing, and monitoring microscopic particles such as cells and biological molecules in solution samples.

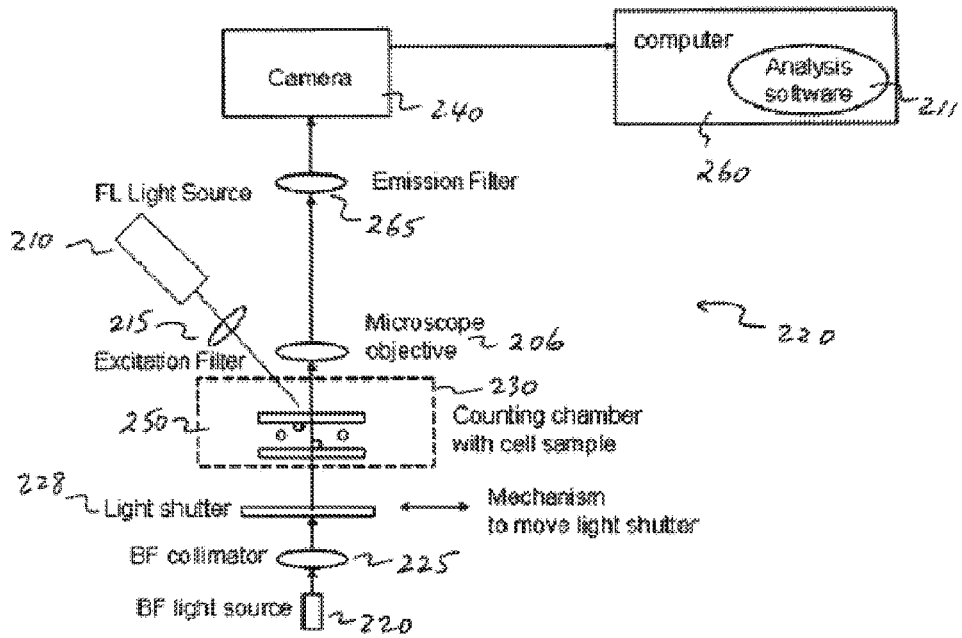

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 4, 6 and 13-15 are cancelled.

Claims 1, 3, 5, 7, 8, 10 and 12 are determined to be patentable as amended.

Claims 9 and 11, dependent on an amended claim, are determined to be patentable.

1. A system for imaging microscopic objects, comprising:
    a covered sample chamber having a fixed depth ranging from about 1 µm to about 200 µm, the covered sample chamber being configured to hold about 1µL to about 1,000 µL of a liquid suspension of microscopic objects to be imaged in a liquid sample, wherein the covered sample chamber comprising an optically clear window allowing exposure of the liquid sample;
    [at least one] *two or multiple sets of* fluorescent light sources *positioned above the sample chamber* capable of providing [a] fluorescent excitation light [beam] *beams* to the liquid sample through the window;
    a bright-field light source capable of providing a bright-field light beam to the liquid sample; [and]
    [at least one] *a* light detection device for detecting a light signal from the liquid sample thereby forming at least one image of the microscopic objects*;*
    *a bright-field light beam narrowing device positioned between the sample chamber and the bright-field light source;*
    *a movable light shutter, located above the bright-field light beam narrowing device and below the sample chamber, for controlling passage of the bright-field light beam to the liquid sample; and*
    *a housing wherein the system is encased, wherein the housing comprises a base on which the bright-field light source is positioned,* wherein
    *the sample chamber is positioned in-line above the bright-field light source,*
    the fluorescent excitation light [beam is] *beams are* at an oblique angle to the bright-field light beam and is oblique to the window's plane of surface, and
    the fluorescent excitation light beam comprises a wavelength ranging from about 300 nm to about 10,000 nm.

3. The system of claim [2] *1*, wherein the system comprises four fluorescent light sources capable of simultaneously providing four excitation light beams having the same or different wavelengths to the sample.

5. The system of claim [2] *3*, having [multiple] *four* fluorescent excitation light beams having the same incident angles in relation to the window's plane of surface.

7. The system of claim 1, wherein the fluorescent excitation light [beam is] *beams are* at an incident angle of about 10° to about 80° in relation to the window's plane of surface.

8. The system of claim [1] *5*, wherein the fluorescent excitation light [beam is] *beams are* at an incident angle of about [45°] *42°* in relation to the window's plane of surface.

10. The system of claim [9] *1*, wherein the microscopic objects are selected from the group consisting of protein surface markers, weak fluorescence labels, and DNA molecules.

12. The system of claim [1] *8*, wherein the fixed depth ranges from about 10 µm to about 100 µm.

* * * * *